(12) United States Patent
Baehre et al.

(10) Patent No.: US 10,278,747 B2
(45) Date of Patent: May 7, 2019

(54) MEDICAL IMPLANT

(71) Applicant: MEDACTA INTERNATIONAL S.A., Ticino (CH)

(72) Inventors: Wolf-Friedrich Baehre, Kusnacht (CH); Kurt Ruffieux, Thalwil (CH)

(73) Assignee: MEDACTA INTERNATIONAL S.A., Ticino (CH)

( * ) Notice: Subject to any disclaimer, the term of this patent is extended or adjusted under 35 U.S.C. 154(b) by 0 days.

(21) Appl. No.: 14/838,462

(22) Filed: Aug. 28, 2015

(65) Prior Publication Data

US 2016/0022332 A1 Jan. 28, 2016

Related U.S. Application Data

(62) Division of application No. 12/664,297, filed as application No. PCT/CH2007/000324 on Jul. 3, 2007, now Pat. No. 9,398,927.

(51) Int. Cl.
*A61B 17/56* (2006.01)
*A61B 17/70* (2006.01)
(Continued)

(52) U.S. Cl.
CPC .... *A61B 17/7097* (2013.01); *A61B 17/00491* (2013.01); *A61B 17/0401* (2013.01); *A61B 17/0487* (2013.01); *A61B 17/122* (2013.01); *A61B 17/68* (2013.01); *A61B 17/70* (2013.01); *A61B 17/7098* (2013.01); *A61B 17/7233* (2013.01); *A61B 17/742* (2013.01); *A61B 17/864* (2013.01); *A61B 17/8805* (2013.01); *A61C 8/0012* (2013.01); *A61F 2/32* (2013.01); *A61B 17/064* (2013.01); *A61B 17/1285* (2013.01); *A61B 17/7059* (2013.01); *A61B 17/8802* (2013.01); *A61B 2017/00004* (2013.01); *A61B 2017/005* (2013.01); *A61B 2017/00831* (2013.01); *A61B 2017/00867* (2013.01); *A61B 2017/0414* (2013.01); *A61B 2017/0488* (2013.01); *A61B 2017/8655* (2013.01); *A61F 2002/30052* (2013.01); *A61F 2002/30065* (2013.01); *A61F 2002/30067* (2013.01); *A61F 2002/469* (2013.01);
(Continued)

(58) Field of Classification Search
CPC ....................................... A61B 17/80–2017/90
See application file for complete search history.

(56) References Cited

U.S. PATENT DOCUMENTS 4,506,681 A * 3/1985 Mundell ............... A61B 17/72
606/101
4,525,147 A * 6/1985 Pitz ........................ A61C 5/50
433/224
(Continued)

FOREIGN PATENT DOCUMENTS

EP 0268179 5/1988
EP 0358601 3/1990
(Continued)

*Primary Examiner* — Zade Coley
(74) *Attorney, Agent, or Firm* — Ference & Associates LLC

(57) ABSTRACT

Medical implant which at least partially comprises a biocompatible, electrically conductive polymer with electrical resistivity p, having the property of being able to be heated and softened by a flow of current through the polymer.

7 Claims, 8 Drawing Sheets

Figure 1:
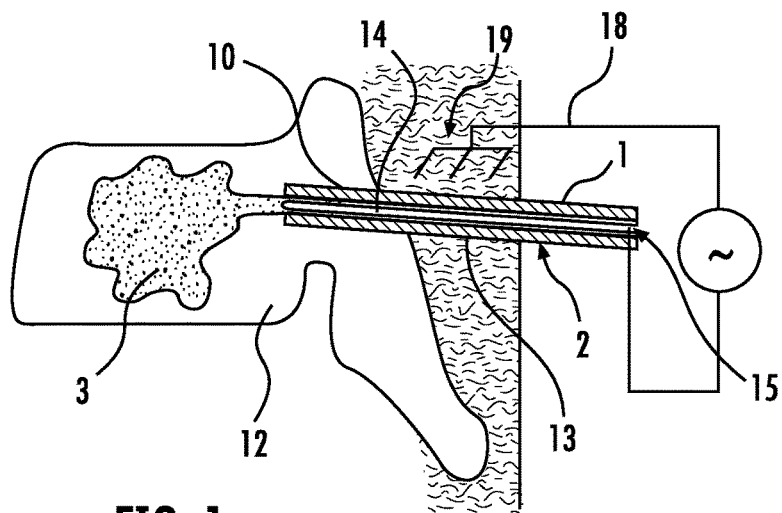

(51) Int. Cl.
*A61B 17/00* (2006.01)
*A61B 17/04* (2006.01)
*A61B 17/122* (2006.01)
*A61B 17/68* (2006.01)
*A61B 17/72* (2006.01)
*A61B 17/74* (2006.01)
*A61B 17/86* (2006.01)
*A61C 8/00* (2006.01)
*A61F 2/32* (2006.01)
*A61B 17/88* (2006.01)
*A61B 17/064* (2006.01)
*A61B 17/128* (2006.01)
*A61F 2/30* (2006.01)
*A61F 2/46* (2006.01)

(52) U.S. Cl.
CPC ............. *A61F 2210/0071* (2013.01); *A61F 2250/0043* (2013.01)

(56) References Cited

U.S. PATENT DOCUMENTS

| | | |
|---|---|---|
| 5,037,442 A | 8/1991 | Wintermantel et al. |
| 5,163,960 A | 11/1992 | Bonutti |
| 5,290,281 A | 3/1994 | Tschakaloff |
| 5,459,298 A * | 10/1995 | Tschakaloff ....... A61B 17/8085 219/221 |
| 5,649,937 A * | 7/1997 | Bito ................... A61B 17/1285 606/139 |
| 5,662,712 A | 9/1997 | Pathak et al. |
| 5,843,186 A | 12/1998 | Christ |
| 5,879,387 A | 3/1999 | Jones et al. |
| 6,080,161 A * | 6/2000 | Eaves, III ............. A61B 17/68 606/329 |
| 6,131,954 A * | 10/2000 | Campbell ............ B29C 65/342 285/21.1 |
| 6,332,885 B1 * | 12/2001 | Martella ............... A61B 17/68 606/286 |
| 6,749,556 B2 | 6/2004 | Banik |
| 6,875,427 B1 | 4/2005 | Devore et al. |
| 7,182,783 B2 | 2/2007 | Trieu |
| 7,294,187 B2 | 11/2007 | Chow et al. |
| 7,740,656 B2 | 6/2010 | Mensah et al. |
| 7,780,705 B2 | 8/2010 | Shaolian et al. |
| 7,824,444 B2 | 11/2010 | Biscup et al. |
| 7,993,404 B2 | 8/2011 | Trieu |
| 2004/0030341 A1 * | 2/2004 | Aeschlimann ... A61B 17/00491 606/232 |
| 2004/0186576 A1 | 9/2004 | Biscup et al. |
| 2004/0230309 A1 | 11/2004 | Dimauro et al. |
| 2005/0008620 A1 | 1/2005 | Shimp et al. |
| 2005/0059972 A1 * | 3/2005 | Biscup ................ A61B 17/686 606/308 |
| 2005/0102017 A1 | 5/2005 | Mattison |
| 2005/0107872 A1 | 5/2005 | Mensah et al. |
| 2005/0234289 A1 | 10/2005 | Anstadt et al. |
| 2005/0234453 A1 | 10/2005 | Shaolian et al. |
| 2006/0282166 A1 | 2/2006 | Molz et al. |
| 2006/0064170 A1 | 3/2006 | Smith et al. |
| 2006/0095138 A1 | 5/2006 | Truckai et al. |
| 2006/0229628 A1 | 10/2006 | Truckai et al. |
| 2006/0241768 A1 | 10/2006 | Trieu |
| 2007/0233250 A1 | 10/2007 | Shadduck |
| 2007/0270833 A1 * | 11/2007 | Bonutti ............... A61B 17/0401 606/28 |
| 2007/0270953 A1 | 11/2007 | Trieu |
| 2008/0195227 A1 | 8/2008 | Boling et al. |
| 2008/0269745 A1 | 10/2008 | Justin |
| 2010/0241229 A1 | 9/2010 | Baehre et al. |
| 2011/0160870 A1 | 6/2011 | Baumgartner |
| 2012/0041557 A1 | 2/2012 | Frigg |

FOREIGN PATENT DOCUMENTS

| | | |
|---|---|---|
| EP | 0696185 | 2/1996 |
| EP | 0698382 | 2/1996 |
| EP | 1000958 | 5/2000 |
| EP | 1421921 | 5/2004 |
| EP | 1454602 | 9/2004 |
| GB | 2181438 | 4/1987 |
| JP | 02167159 | 6/1990 |
| JP | 08506027 | 7/1996 |
| JP | 9511666 | 11/1997 |
| JP | 2007511329 | 5/2007 |
| WO | 9411058 | 7/1994 |
| WO | 9528124 | 10/1995 |
| WO | 2001047337 | 7/2001 |
| WO | 2002039875 | 5/2002 |
| WO | 2004016205 | 2/2004 |
| WO | 2004034917 | 4/2004 |
| WO | 02069817 | 5/2005 |
| WO | 2006002569 | 1/2006 |
| WO | 2006069677 | 7/2006 |
| WO | 2007092869 | 8/2007 |
| WO | 2008079864 | 7/2008 |
| WO | 2009013752 | 1/2009 |
| WO | 2009036576 | 3/2009 |
| WO | 2011066522 | 6/2011 |
| WO | 2012021148 | 2/2012 |

* cited by examiner

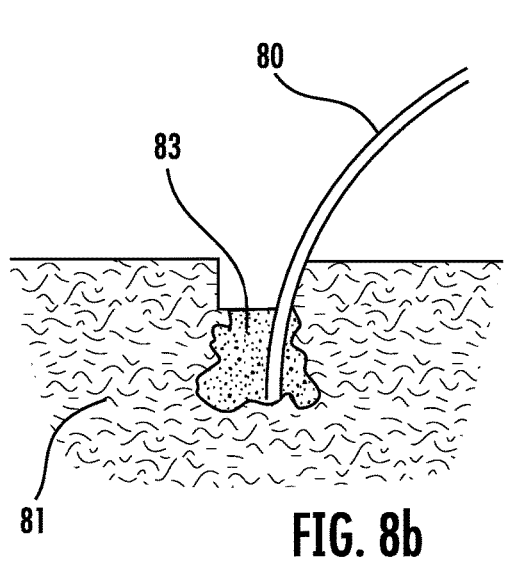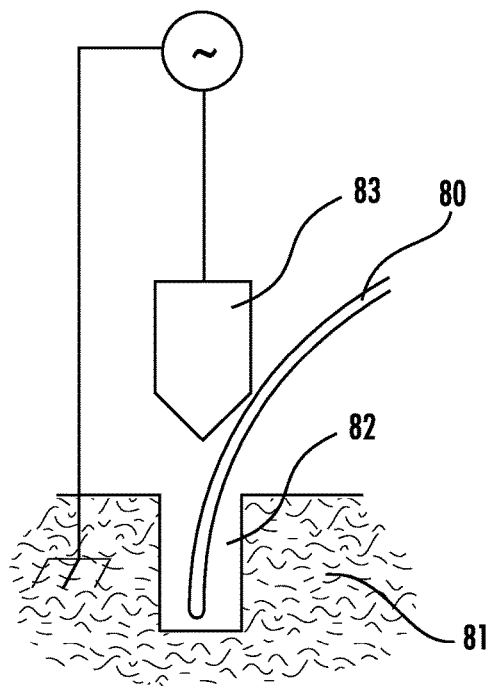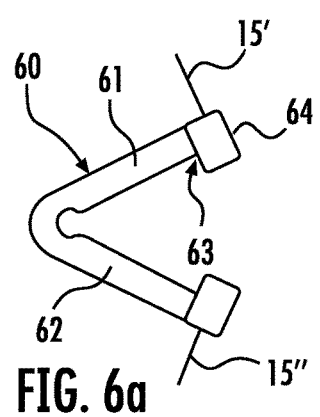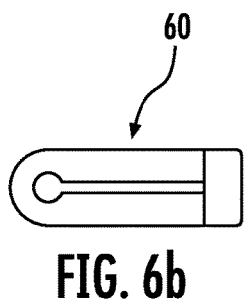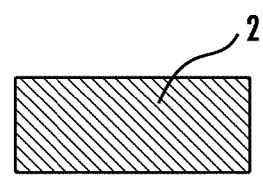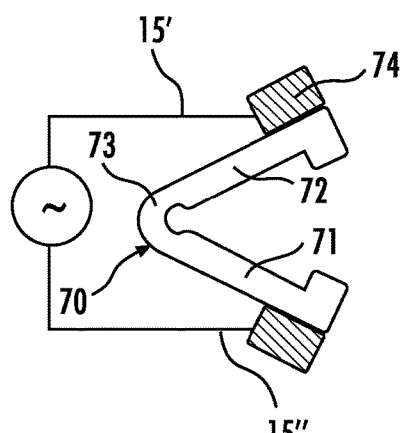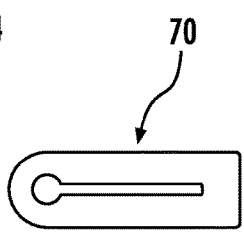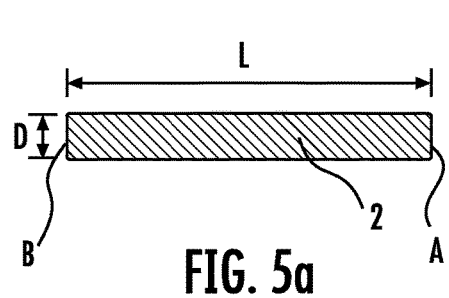

MEDICAL IMPLANT

The invention refers to a medical implant according to the main concept of patent claim 1, a device comprising a medical implant according to the main concept of patent claim 70, an osteosynthesis process according to the main concept of patent claim 71 and a further osteosynthesis process according to the main concept of patent claim 81.

The use of biocompatible, thermoplastic materials for osteosynthesis and similar processes for fastening purposes on human or animal bones is a known state of the art and has been attempted in various ways, for instance by an external application of heat as in a hot gluing pistol (for instance U.S. Pat. No. 5,290,281), or by liquefying a polymer by ultrasound wave energy according to WO2006/002569 WOODWELDING. These techniques are however affected by disadvantages: the warming-up by external heat sources—as in a hot gluing pistol—means that an implant must be inserted very quickly, so as not to cool off again while undergoing the connection with the bones, because it typically presents only a small thermal capacity and the thermoplastic material can for instance penetrate into the interspaces in the bone only in a softened condition. As soon as the material has cooled off, no further connection with the bone occurs. Even the necessary excessive warming-up of the thermoplastic materials—to prevent a premature solidification—is disadvantageous, because it causes damage to both the material and the (bone) tissue. Moreover, the heating—as would ideally be desirable—does not merely heat-up the transition zone to the tissue in the implant, but also areas which should not be heated and softened, because they are situated between the heat source and the target area in the plastic material. The subsequent removal of the cooled-off thermoplastic material is difficult and hardly feasible without an excessive warming-up of the surrounding tissue. These disadvantages are also present at an irradiation with an electromagnetic radiation, for instance infrared light.

In case of a liquefying with a directly applied ultrasound energy, the problems mentioned above in connection with an external heat source are actually not present, but the grave disadvantage consists of the fact that the bone must offer a mechanical resistivity sufficient to soften the (vibrating) thermoplastic material at the contact zone with the bone, and that there is a risk of mechanically damaging the bone. In principle, a bone structure of the greatest possible density must be available in order to guarantee a safe fusing-on of the thermoplastic material. At the very point where a good fusing-on of the polymer in the bone would be desirable, especially in the zone of an osteoporotic bone, the fusion of the polymer can only be achieved in an unreliable manner, and in the case of a missing fusion no mechanical connection occurs. A further disadvantage of the ultrasound technique is the fact that after the polymer's hardening following a completed connection with the bone a liquefying is no longer possible, meaning that the implant cannot be removed again without major effort (drilling open, tearing out, fusing, and awaiting degradation).

This is where the invention will provide a remedy. The task underlying the invention is to create a medical implant capable of being softened by developing internal heat. The risk of damaging the tissue through excessive heat (mostly explained in the following on an example in bones) is reduced, especially in comparison to the state of the art, which uses an en external heat source. The fixation result's dependence on the quality of the bones is considerably reduced. The electrically conductive polymer can be re-softened by using electrical current, and at least partially be removed.

The hazards in employing the medical implant according to the invention are reduced because the actual evolution of heat (to soften the polymer) is generated inside the implant and in the transition between the implant and the. The release of energy by the current, at the point where the implant contacts the bone, is concentrated inside the implant, and because of the relatively smaller functional cross-sectional surface of the conductive implant, the greatest evolution of heat, at greatest current density, occurs at that point (ideally at the contact point). This effect can be further reinforced by a suitable design of the implant and of the electrode. It has also been demonstrated that after fusing, a polymer of proper composition can reduce its electrical resistivity up to a factor of $10^3$-$10^8$, and therefore cannot significantly be heated further by the flowing current. To a certain degree the system is therefore self-regulating, and spares the surrounding tissue. In other embodiments, a correspondingly increased resistivity has under certain circumstances likewise proved advantageous (for instance for the fusing of polymer particles with each other).

The bone can further be protected by choosing a conductivity of the implant or of the transition from the implant to the bone which is lower than that of the bone, so that the latter warms-up less. If necessary the bone can also selectively be cooled off by using cooling elements, rinsing fluids or gas/air flows.

The medical implant according to the invention can be realized in various implant forms, in particular as a screw, pin, clip, prong, plate, nail, spiking wire, cage, pedicle screw (or nail), piercing, skin attachment, medicament carrier, gene material carrier, bioactive factor carrier (for instance growth factors, bone formation promoting substances, pain killers, etc.), as carriers of other implants, as a dowel, clamp, pearl, dental implant, dental root implant, hose, tube, thread, thread in a hose or tube, tissue, web, skeleton, stocking, band, loose fibers, fibrous knot, fibrous flocks, granulate, chain, and anchor with or without a threading eyelet. After the implantation, the implant can also serve in or on the body for diagnostic, stimulation or monitoring purposes. The same elements can also be heated by an incorporated wire, a pin or other current carrier (made of the same or of another material, for instance metal), which serve as temporary current suppliers but not directly for warming-up purposes, and can later optionally be removed. These current conductive elements can later also be left in place and be designed conformed to be biologically resorbable (for instance, made of magnesium).

The invention solves the intended task by using a medical implant which exhibits the characteristics according to claim 1, by using a device for fixating bones or bone fragments presenting the characteristics of patent claim 70, an osteosynthesis process according to patent claim 71, and a further osteosynthesis process according patent claim 81.

The medical implant according to the invention utilizes the effect that under a flowing current, a heat is generated in the electrical conductors or at the transition between electrical conductors at the point of the largest (for instance ohmic) resistivity (in a current circuit). The specific characteristic of the medical implant according to the invention is that an electrical current is used for warming-up a polymer, preferably a thermoplastic material that is electrically conductive in itself, or can be made electrically conductive by additives. With the aid of such a thermoplastic, electrically conductive polymer it is surprisingly possible, through a softening of the thermoplastic material and a suitable implant design and preferably during a surgical operation, to achieve mechanical connections on, toward and with human or animal bones. Because of the fact that the greatest evolution of heat occurs at the point of the greatest resistivity in a current circuit and therefore the greatest voltage drop, it is also possible to specifically control the warming process so that the material softens up only at certain preferred points. It should be observed that the current tries to find the path of least resistivity, this forming a current circuit. The location of greatest resistivity corresponds to the location of the greatest resistivity in such a current circuit, and the implant is to be designed in a manner such as to force the current to flow through desired regions of the implant, without draining away in other directions. The implant material acts for the rest as a partial insulator, is crossed by little current and correspondingly little softened. The human and animal body, and in this context especially the bone, has proved to be a very suitable electrical conductor for acting as an onward transmitter of the electrical current circuit, and in the specific application described here warms-up surprisingly little. This is additionally favored by using polymers which are reducing their resistivity in a fused condition.

In a particular application, the implant can thus be connected to one pole (in case of a direct current) or to one phase conductor (in case of alternate current, radio frequency current) of the current circuit, while applying the other pole or zero conductor to the body through a large surface-area electrode. The current flows over one electrode to the implant, through the implant and the contact area or point with the body, for instance the bone in the same, onward through the same and then exits again through a neutral electrode. The current will warm-up and soften the implant at the desired location of greatest electrical (ohmic, inductive, capacitive or other) resistivity or voltage drop in the current circuit.

Alternatively the current can also, without crossing the patient's body, be made to pass through the implant between two suitably applied poles (in a "bipolar" manner), so as to again warm up, soften or fuse the implant at the point or region of greatest resistivity.

The following definitions apply to the following terms frequently employed in the entire description:

Energy: For the warming-up and softening of the implant the invention utilizes the current flowing through the implant, as suitably applied by electrodes. The current may be an ohmic current, wherein electrons are flowing in a metal like as under direct current. Protons or other loaded particles can also be considered as carriers of charges to be moved. However, the current may also be of an ion-shifting type, such as occurs when a current flows through a saline solution. Chemical reactions capable of allowing a shifting of electrons or charges like in a battery are also possible. In particular, this also includes an inductive or capacitive current, and shifting capacitive charges are the preferred current mode in this application. The current may also be flowing in diverse ways, for instance in bones as an ion current and proton current, in a polymer for instance at the same time as an electron current. The current or electrical voltage may be employed as a direct current, alternating current or, preferably, as a high frequency alternating current (radio frequency). Even a sparking can be used for the application according to the invention.

Fusing/softening/plasticizing: The terms of fusing, softening or plasticizing of the implant material in the sense of the Invention are intended to mean the softening of the implant by the current flow in itself or by the heat generated by the same, until the implant, which could previously not be plastically deformed in the body in a useful manner (typically by hand), can be allowed to deform by applying a moderate force (typically by hand) and to be used according to the invention.

Resistivity and conductivity: The terms "electrical resistivity" or "conductivity" are, for the respective type of current used, taken to mean the surface resistivity (Ohm/square), the volume conductivity (S/cm) or the absolute resistivity. These definitions are interchangeable and not to be understood in a limiting manner. The invention aims in particular at an adequate conductivity of the material, so as to achieve a sufficient flow of current for the necessary softening, a certain resistivity is otherwise needed to achieve an adequately large voltage drop and consequently a sufficiently large release of energy in the implant to soften the same. It is ideally desirable to strive for a markedly lower conductivity than in the surrounding tissue, so as to spare the latter (low warming there). Finally, the conductivity is a function of the current type, voltage, material cross section and volume conductivity/resistivity of the material itself, and must be adjusted for the relative application. In the complex alternating current calculation, the concept "resistivity" is replaced by a complex entity, the so-called "impedance" with its components "resistivity R" and reactance X".

Neutral electrode: In case of an alternating current, the term "neutral electrode" is taken to mean the pole connected with the neutral conductor or grounding.

Monopolar: The term "monopolar" is to mean an application wherein the current discharge (through a neutral conductor, "neutral electrode" or grounding occurs on the skin or elsewhere on the body through a large surface electrode), and the alternate current is typically fed-in through the implant. The poles can also be inverted.

Bipolar: The term "bipolar" Is in this case taken to mean the direct input and output of the current through two electrodes applied in the next neighborhood of the implant (for example, electrical tweezers with two poles). The advantage lies in this case in the fact that the flow of current through the body can be reduced or avoided.

Organic semiconductors: "Organic semiconductors" represent a group of conductive polymers, on one hand the group of charge-carrying complexes ("charge transfer complexes") and on the other hand the polyacetylene, polypyrrole, polyanilin etc. groups and their derivatives. These polymers can always be present in any mixtures or in their pure trans- and cis-forms.

Self-conductive polymer: This is to mean polymers capable of being conductive without using other additives, which at this point additionally includes co-polymers (for instance a co-polymer between lactide and pyrrole, which are also electrically conductive.

Polymer made conductive: This is to mean polymers that are fitted with additives, typically a powder in a micro- or nanometer range, self-conductive polymers, low molecular weight substances or liquids made electrically conductive by these additives. To be explicitly excluded from this group are polymers that are fitted with other macroscopic structural elements, namely fibrous mats, endless fibers, wires, threads, needles etc. so that the polymer itself is no longer conductive but only the structural element additionally present in the polymer, whose warming softens the surrounding polymer.

The medical implant according to the invention allows solving various tasks, some of which will be described in greater detail, as follows:

Task A: Selective or Global Warming and Softening or Liquefying of Medical Implants by Using Electrical Currents During their Implantation.

In this case, in the example of straight pin a current circuit is established by using an electrode whose one end (on the side turned away from the bone) is connected to an electrically conductive pin, through the pin itself, then over the point of contact to the body (for Instance the bone) and over the body to a neutral electrode. At the point of contact between the implant and the bone the voltage drop is greatest (greatest resistivity) and the thermoplastic material warms-up and turns soft up to a liquid. The core of the pin is conceived so as not to warm up or only partially so, and to remain hard. The pin can then be driven into a pre-drilled hole that can for instance be undersized, and the warmed-up, soft and conductive thermoplastic material is pushed into the interspaces in the bone. After switching off the current, the thermoplastic material cools off and quickly hardens (<1-2 minutes), and the mechanical connection is thus established.

Task B: Selective or Overall Warming-Up of a Thermoplastic Material Containing Implant to Achieve a Deformation During its Implantation.

In this case, a conductive pin on its way is provided with a zone containing of higher resistivity and returned inside the current circuit. The pin will warm-up in the zone with the greater resistivity. The pin can deform at this point.

Task C: Achieving a Local Fixation of an Implant Comprising a Conductive Thermoplastic Material in the Body.

Through a suitable production process, for instance by injection molding, the pin is provided with a residual stress. Thanks to the warming-up of the entire pin, the thermoplastic material is relaxed and the pin shortens and increases in diameter, thus leading to a fixation in or on the surrounding tissue.

Task D: Achieving a Local Connection Between Several Implants Comprising a Conductive Thermoplastic Material by Welding them to Each Other.

This consists of connecting two thermoplastic implant elements, which can be separately inserted into the body. This action must guarantee that the necessary current can flow through both (or several) implant elements to be connected. After inserting the two (or several) implant elements, the current is admitted, the implant elements soften at their point of contact and can be joined by applying pressure. This may also allow gluing up a thread in order to forgo a knot, while passing through the current directly through the connection point with a bipolar current source.

Task E: Lining of Hollow Organs.

The blood vessels, intestines, stomach, bones, urinary tract, bladder, uterus, gall bladder, tubes, vagina, urethra etc. can be lined with a medical implant produced from the implant material described, for instance in the form of a stent, and be for example mechanically augmented by the same. In this connection, a stent subject to a residual stress can also expand due to warming, or the stent can, in the softened condition and while resorting to mechanical pressure, for instance by expanding a balloon, be deformed.

Task F: Clamping or Enveloping Soft Tissues or Bones

A stomach strip can for Instance be formed from the implant material (as an open ring), made deformable by supplying current and then connected to a closed ring. A polymer strip can likewise be employed as a forming material.

Task G: Skin Closing

In particular, polymers having a preferably low fusion point can also be glued directly to the skin, for instance for a mechanical skin closing or for instance as an ECG electrode.

Task F: Production of Implants that can be Changed after Inserting into the Body, by Cutting the Implant Material Apart.

The implant material used and described here can also be employed for the purpose of producing implants that can be selectively cut apart or opened by using electrical current. In this manner, a thread may for instance also be cut by an electrical cautery, in particular at great voltage or current or preferably with a small but "sharp" electrode. Dented-in or fused-in pins can thus for instance be cut off at the bone surface or modeled onto the same, until they fit flat on the surface of the bone. Medicament carriers can thus be opened to release their active ingredients.

Any kind of current is suitable for the softening or liquefying of the medical implant according to the invention, in particular direct current, alternating current, inductive current (microwave), three phase current, multiple phase/multiple pole current, and typical cautery current patterns.

The transmission of current can be realized in various ways, for instance as a direct transmission of current by using two electrodes ("bipolar") passing through the thermoplastic material or in a "monopolar" manner through the body, as a transmission of current by using a capacitive, ohmic or ionic current, and as a transmission of current by sparking (arching). Suitable current sources are for instance sources such as an electrical cautery, a VAPR (product name, Johnson & Johnson) or a microwave transmitter.

In case of a radio frequency alternating voltage, the preferred frequency is an alternating voltage of >20 kHz, typically >300 kHz up to 3 MHz (radio frequency). Typical average current source: for small pins or fixation elements (diameter 0.1-5.0 mm): about 0.1-50.0 Watt, preferably 0.5-10.0 Watt. For the fixation of large prostheses or for the filling of large bone defects 1-2,000 Watt.

The peak power during a single applied pulse may attain 5 kW and more.

Typical electrical voltage: 20 Volt-3,000 Volt, preferably 20-300 Volt.

Typical current intensity: 0.01-100.00 Ampere, preferably 0.05-10.0 Ampere.

Alternating current form (radio frequency alternating current): sinusoidal, rectangular, trapezoidal, etc., asymmetrical or symmetrical, pulsed or continuous.

Typical pulsation lengths: 0.1 ms-5.0 ms.

In particular, it is to be taken into account that the current intensity can be regulated, by measuring the resistivity/impedance of the current circuit (Ohm), current flow (Ampere), power output (Watt) or by direct (for instance heat sensors) or indirect (for instance infrared camera) measurement of the heat of the implant or of the surrounding tissue. This allows preventing an excessive warming-up, and provides a careful treatment of the implant as well as of the tissues or other implants (threads). Electrical cautery means frequently already offer a regulating mechanism than can also be used for this purpose (for a constant or modulated power output). Another possibility consists of measuring the mechanical resistivity of the implant during the deformation, and to regulate the electrical power output accordingly. As an additional regulating effect it is also possible to employ the polymer's resistivity change while warming-up or softening, whereby the warming-up can be controlled (see above in the text).

The biologically compatible and biodegradable polymers for the medical implant according to the invention can be chosen from the following group: poly-alpha-hydroxyester, polyorthoester, polyanhydride, polyphosphazines, poly(propylenefumarate), polyesteramide, polyethylenefumarate, polylactide, polyglycolide, polycaprolactone, trimethylenecarbonate, polydioxanone, polyhydroxybutyrate, as well their copolymers and mixtures.

The biologically compatible, non-biodegradable thermally plastic polymers for the medical implant according to the invention can be chosen from the following group: polyethylene, polystyrene, polyester, polypropylene, and polysulfone.

The thermally plastic polymers for the medical implant according to the invention can for instance be chosen from the following group of materials, while reducing the softening point with additives, depending on the indications:

Acrylonitrile-butadiene-styrene (ABS), polyacryle, celluloide, cellulose acetate, etylenevinyl acetate (EVA), ethylenevinyl alcohol (EVAL), fluoroplastic, ionomere, polyacrylate, polyacrylonitrile, (PAN or acrylonitrile), polyamide (PA or Nylon), polyamidimide (PAI), polyaryletherketone (PAEK or ketone), polybutadiene (PBD), polybutylene (PB), polybutylene terephtalate (PBT), polyethylene terephtalate (PET), polycyclohexylene dimethylene-terephtalate (PCT), polycarbonate (PC), polyketone (PK), polyester, polyethylene (PE), polyetheretherketone (PEEK), polyetherimide (PMP), polyphenyleneoxide (PPO), polyphenylenesulfide (PPS), polyphtalamide (PPA), polypropylene (PP), polyurethane (PUR), polysulfone (PSU), and polyhydroxy ethylmethacrylate (PHEMA).

The desired thermal stability of individual zones of the medical implant can be varied by the choice of the materials depending on the conductivity, point of fusion as well as specific electrical resistivity of the individual materials.

If the thermoplastic material intended or the medical implant according to the invention is in itself not conductive at all points, it can be modified, by incorporating suitable electrically conductive elements (for instance cables, electrical conductors, cores made of steel or titanium) at least partially into an electrically conductive thermoplastic material, and thus be designed as a current supplying electrode. In this connection the zone of contact to come into electrical contact with the patient's body can be coated with the thermally conductive thermoplastic material wholly or partially. If the contact zone is coated with a conductive thermoplastic material only partially, then the remaining surface should preferably not be electrically conductive. This can be done by appropriately choosing the material or by an appropriate coating, such as for instance with hydroxyapatite or other, for instance osteoconductive, osteoinductive or osteogenic materials.

The process steps used in applying a medical implant according to the invention are now described in closer detail:
a) Preparation of the bone, for instance by inserting a borehole;
b) Setting the fixation element into the borehole;
c) Warming-up the (thermoplastic) implant polymer;
d) Pressing the implant into the tissue to be fixated; and
e) Allowing the implant to cool and solidify, which can be assisted for instance by active cooling.

In a preferred form of embodiment the polymer is chosen so that the softening occurs below a warming-up temperature of 250° C.

In another form of embodiment the softening occurs below a warming-up temperature of 150° C., preferably below 100° C. The advantage of this form of embodiment lies in the fact that it allows an implantation into the (human or animal) body that is sparing the tissues.

In a further form of embodiment, no structural elements other than the polymer itself are provided for the warming-up of the implant. This form of embodiment is distinguished by the increased simplicity of fabricating and applying the implant.

In another form of embodiment the medical implant comprises means for the fastening of an electrode.

In yet another form of embodiment the means consist of a recess or an elevation on the surface of the polymer.

In a further form of embodiment the means consist of a material with an electrical resistivity $p_M < p$. The advantage of this form of embodiment lies in the fact that the electrical current is preferably flowing through the polymer and not through the means used for fastening the electrodes, thus preventing the latter from fusing with the rest.

In another form of embodiment the polymer is a semiconductor, preferably an organic semiconductor.

In one more form of embodiment the polymer comprises molecular chains with extensively conjugated double bonds.

In a further form of embodiment the specific electrical resistivity $\rho$ is greater than 500 Ohm-cm, preferably greater than 1,500 Ohm-cm.

In another form of embodiment the specific electrical resistivity $\rho$ is greater than 3,000 Ohm-cm, preferably greater than 10,000 Ohm-cm.

In a further form of embodiment the polymer has a specific surface resistivity of at least $10^{-1}$ Ohm/square, preferably at least $10^2$ Ohm/square.

In another form of embodiment the polymer has a specific surface resistivity of at most $10^{12}$ Ohm/square, preferably of at most $10^7$ Ohm/square.

In one more form of embodiment the polymer has a volume conductivity of at least $10^{11}$ S/m, preferably of at least $10^4$ S/m.

In another form of embodiment the polymer has a volume conductivity of at most $10^1$ S/m, preferably of at most 100 S/m. The volume conductivity is typically at most 0.1 S/m.

In a further form of embodiment the electrical resistivity in the implant is reduced by the fusion of the polymer or the warming-up of the implant.

In an additional form of embodiment the electrical resistivity in a fused or warmed-up condition of the implant is reduced by at least a factor of 0.5, preferably by a factor of 10.

In an additional form of embodiment the electrical resistivity in a fused or warmed-up condition of the implant is reduced by a factor of >100. The advantage of this form of embodiment lies in the fact that the areas already fused in this manner are no longer warming-up and are thus sparing the surrounding tissue.

In a further form of embodiment the electrical resistivity in the implant is increased by a fusing of the polymer or a warming-up of the implant.

In one more form of embodiment the electrical resistivity in a fused or warmed-up condition of the implant is increased by a factor of at least 0.5, preferably by a factor of 10.

In another form of embodiment the polymer is isotropic.

In another form of embodiment the polymer is anisotropic.

In a further form of embodiment the polymer is a thermoplastic material.

In one more form of embodiment the thermoplastic material is taken from the group of polyacetylene, poly(ethylenedioxithiphene), poly(phenylinvinylene), polyarylene, polyspiro-bifluorene, polythiophene or polypyrrole.

In another form of embodiment the thermoplastic material is chosen from the following groups:
Thermoplastic polymers that are electrically conductive in themselves;
Mixtures of non-electrically conductive (matrix) polymers with fillers or additives allowing conductivity;
Copolymers composed of electrically conductive and electrically non-conductive polymers;
Conductive polymers, wherein the application of electricity or heat can induce a chemical reaction (for instance a polymerization) or a physical reaction (for instance a geometric change);
Conductive non-polymers, wherein the application of electricity or heat can induce a chemical reaction (for instance a polymerization) or a physical reaction (for instance a geometric change). Such materials can be of an organic or also non-organic nature, for instance ceramic, gel, collagen or chemical substances in the form of a liquid or a paste-like composition, which hardens again after thermal activation.
Combinations of the materials mentioned above.

In another form of embodiment the medical implant also comprises, apart from the polymer, implant elements made up of other materials, which are preferably chosen from the following groups: metals, carbon, ceramic, PEEK, non-thermoplastic polymers preferably chosen from the group of the polymethylmetacrylates, and/or inorganic materials such as calcium phosphate, calcium sulphate or bone cement.

In another form the polymer is electrically conductive in itself.

In one more form of embodiment the electrical conductivity of the polymer is achieved by an appropriate doping.

In a further form of embodiment the polymer is combined with an electrically conductive ceramic, in particular one having a glass-like or amorphous structure.

In still another form of embodiment the polymer is obtained from a non-conductive polymer by using electrically conductive additives. Suitable additives are for instance: particles of soot ("carbon black"), preferably 3-50%; coal fibers of a length of at most 1 mm, preferably 3-50%, with the most homogeneous possible distribution in the polymer; coal nanotubes, preferably 0.1-5%; metal particles, especially of iron, titanium, gold, magnesium, steel; salts, especially NaCl, barium, magnesium salts; proteins, bone material; oils; silicates. All conductive additives can be added in the form of spheres, flocs etc.

In another form of embodiment the electrically conductive additives consist of any possible, electrically conductive solid or liquid material in the form of particles, granules, and particle accumulations of any external shape.

In a further form of embodiment the electrically conductive additives are chosen from the following materials:
Metallic materials, for instance iron, magnesium, gold, silver, alloys or amalgams;
Carbon particles, for instance soot, carbon nanotubes, Fullerene;
Salts or substances capable of quickly attracting water, so as to allow the flow of electricity in the necessary amount. Such salts may for instance consist of sodium chloride, sodium sulphate or magnesium salts.
Electrically conductive polymers, for instance polymers chosen from the pyrrole, aniline, dialkylfluorine, thiophene or ethylenedioxythiophene groups.
Biocompatible oils, for instance silicones;
Aqueous solutions, preferably saline solutions.

The quantity of fillers/additives must be adapted to the intended usage, so as to adapt the electrical conductivity to the desired purpose, for instance to adapt the material's electrical resistivity so that the warmed-up material becomes thermoplastic, capable of flowing or even liquid, or that the material hardens upon priming a certain chemical reaction.

In an additional form of embodiment the polymer presents an open-pore structure.

The advantage of this form of embodiment lies in the fact that it favors the healing of bones and that it allows electrically conductive liquids, gels or other materials to be held in place.

In one more form of embodiment the polymer presents capillary channels. This makes it possible to achieve the advantage that it allows the penetration of saline solutions from the body or other liquids, so as to modulate the conductivity In another form of embodiment the medical implant consists of a homogeneous material.

In a further form of embodiment the homogeneous material does not possess an inner structure.

In one more form of embodiment the polymer is present in the form of an implant coating.

In an additional form of embodiment only a portion of the implant's surface is coated with the polymer.

In a further form of embodiment the polymer comprises areas having a different specific electrical resistivity $\rho$, especially in the form of surface coatings.

In another form of embodiment the coatings present a variable coating thickness.

In one more form of embodiment the entire implant or only the polymer is partially coated with electrically non-conductive materials. This makes it possible to achieve the advantage that this execution of the coating allows defining a path for the passage of the current. The con-conductive coating should serve as an insulation and prevent a short circuit.

In another form of embodiment the electrically non-conductive material presents osteoconductive, osteoinductive or osteogenic properties.

In a further form of embodiment the electrically non-conductive material is a polyactide or hydroxyapatite.

In another form of embodiment the polymer comprises a mixture of at least two electrically conductive thermoplastic materials compatible with the body. This form of embodiment is distinguished by areas having various conductivities at a constant implant form. The electrically conductive thermoplastic material may be present in the form of a polymer, gel, paste or wax.

In one more form of embodiment the medical implant presents a solid form. The advantage of this form of embodiment lies in the fact that an external force can be applied on the implant in a better manner.

In a further form of embodiment the polymer is present in a granulated form. This makes it possible to achieve the advantage that the polymer can be filled into the interspaces, gaps or hollows in this manner, and be hardened there.

In another form of embodiment the medical implant is produced from fibers, where the polymer preferably serves as a coating for the fibers. The fibers can be braided, woven or twined and be present as individual threads, as a net, cloth or bag. The advantage of this form of embodiment lies in the fact that the textile/fibrous implant can thus be turned into the desired shape and then hardened or glued under the flow of current.

In a further form of embodiment the medical implant Is present as an open-pore foam or sponge.

In another form of embodiment the medical implant is conformed as a bone fixating element, preferably in the form of a bone screw, bone rod, bone dowel, pin, plate, dowel, hose (tube), thread, thread in a hose/tube or anchor (with a threading eyelet).

In an additional form of embodiment the polymer is conformed as a bar and presents a longitudinal central hole, which is useful for a longitudinally sliding reception of a metallic rod connectible to an electrode, or of a rod firmly connected to an electrode.

In another form of embodiment the medical implant comprises a metal pin or a metal wire receivable in a longitudinal hole, which is fitted with an Insulation except in a partial section at the ends.

In a further form of embodiment the polymer is conformed as a bar and comprises a peripheral, electrically non-conductive insulating layer.

In a further form of embodiment the polymer is conformed as a bar and comprises an outer bushing made of a second, conductive polymer with a higher resistivity.

In another form of embodiment the polymer is conformed as a pearl and releasably connectible with an electrode in the form of a wire.

In one more form of embodiment the medical implant is conformed as a dental Implant or dental root implant.

In a further form of embodiment the polymer is at least partially present in a softened condition.

In an additional form of embodiment the softened condition is generated by a current passing through the polymer.

In one further form of embodiment the electrical current is generated by an external source of current.

In another form of embodiment the source of current is a source of alternating current.

In one more form of embodiment the polymer can be warmed-up and softened by an alternating current with a frequency v higher than 20,000 Hz, preferably higher than 300,000 Hz.

In another form of embodiment the polymer can be warmed up and softened by an alternating current of a current intensity I between 0.001 and 10 Ampere.

In another form of embodiment the polymer can be warmed up and softened by an alternating current of a voltage U between 20 and 300 Volt.

In another form of embodiment the polymer with a volume V can be warmed-up and softened to be softened by an alternating current with a power density $P=0.005-5$ Watt/mm$^3$ within 0.1-10 seconds. The energy thus applied corresponds to $E=0.0005-50$ Watt*seconds/mm$^3$.

In one more form of embodiment the polymer does not present a uniform conductivity, and the latter is preferably smaller on the surface of the implant than in the interior of the implant. In both forms of embodiment (bipolar and monopolar) the implant according to the invention can to the outside present areas of electrical insulation, meaning that in a pin used in a monopolar manner the electrically conductive shaft can for instance be insulated by a non-conductive layer, and that for instance only the tip of the implant can be in electrical contact with the body. It is thus possible to achieve that the implant softens up for instance first at the tip and can thus be fused into the bone, while the shaft of the pin maintains its stability. This allows achieving the advantage that a selective warming-up of the polymer is possible, meaning precisely at the point where it is expected to fuse, liquefy or soften due to the flow of current, preferably at the surface of the implant that is in contact with the patient's tissue.

In another form of embodiment the electrically conductive polymer of the medical implant does not comprise any internal structural elements, structures or fibers that are impacted from the outside by electrical energy and are thus warmed-up by the same.

In one more form of embodiment, the generation of heat occurs in an electrically conductive polymer of the medical implant only by a current flowing through the electrically conductive polymer.

In an additional form of embodiment, the entire electrically conductive polymer of the medical implant is crossed by a flow of current, so that a homogeneous warming-up of the same takes place.

In a further form of embodiment the entire electrically conductive polymer of the medical implant is crossed by a flow of current, so that a non-homogeneous warming-up of the same takes place.

In a preferred form of embodiment of the process the patient's body is in itself used as a neutral electrode of the current circuit.

In another form of embodiment of the process the medical implant is switched into the current circuit between two bones. This is suitable for a bone-thermoplastic material-bone application of the medical implant.

In one other form of embodiment of the process one electrode of the current circuit is connected with a bone fragment and the second electrode with the associated bone or otherwise with the patient's body.

In another form of embodiment of the process, one electrode of the current circuit is connected to the bone fragment and the second electrode to the medical implant inserted between the bone fragment and the bone.

In another form of embodiment of the process the implantation location is a borehole in a bone.

In a further form of embodiment of the process, the medical implant is, in a non-softened condition, oversized with respect to the borehole in the bone.

In a further form of embodiment of the process, the medical implant is, in a non-softened condition, not oversized with respect to the borehole in the bone and has an internal residual stress. The application of a residual stress can for instance occur during the fabrication process, for instance by injection molding.

In another form of embodiment of the process, the electrically conductive polymer is inserted through an insulated cavity of an implant in the form of a rod, and preferably comprises an electrically conductive core.

In one more form of embodiment of the process, the electrically conductive polymer is inserted into a cavity with radially exiting holes.

In a further form of embodiment, the medical implant is employed for a plastic vertebral surgery.

In an additional form of embodiment of the process, the medical implant is employed for the locking and/or centering of implants, in particular for medullary nails after their inserting into the bone.

In another form of embodiment, the polymer is chosen so that the softening occurs above a warming-up temperature of 40° C.

EXAMPLE 1 (Plate Osteosynthesis)

An resorbable osteosynthesis plate of 1 mm thickness made of a poly-D,L-lactide was applied to the bone fragments to be fixated, and the necessary holes were drilled into the bone. In this example the plate was fitted with holes for 2.0 mm screws. Holes of 1.7 mm size were drilled into the bone. An electrically conductive pin of 2.0 mm diameter was then set up on an electrode connected to a commercially available electrical cautery. The pin consisted of poly-D,L-lactide admixed with 15 percent of carbon black.

The patient was connected to the neutral electrode of the cautery in a conventional manner. The pin was set up on the pre-drilled hole through the screw hole in the plate and subjected to a current (power of 5 Watt). The current flowed through the electrically conductive pin and warmed-up the same. Because the largest electrical voltage drop occurred at the transition from the bone to the pin, the greatest warming-up occurred here in the pin, whereby the pin was softened up, especially at its surface. By exerting a soft pressure on the electrode, the pin could then be pushed into the hole that had been pre-drilled in the bone, and the thermoplastic material flowed into the accessible inter-trabecular inter-spaces in the cancellous bone. After switching off the current, the polymer cooled off and hardened in less than 1 minute. The pin fitted with a somewhat oversized head (meaning larger than the borehole in the plate) was now locking the plate at the desired point.

EXAMPLE 2 (Plate Osteosynthesis)

In a variant of Example 1, a bone plate was used which had likewise been produced from the same electrically conductive thermoplastic material as the pin described above. The pin was inserted as in the above example. As soon as the head of the pin had come in contact with the plate, a fusion between the plate and the pin also occurred at this point, as in the zone of the hole the plate was likewise electrically conductive and a fusion between the plate and the head was achieved at that point. After cooling the pin and the plate were firmly connected to each other, and the connection was thus locked at a stable angle.

EXAMPLE 3 (Bone Anchor)

The problem to be solved was in this case to fixate a thread in the bone, so as to lock up a tendon or other bone element with a thread. For this purpose a hole of a diameter of 3 mm and a depth up to 15 mm was drilled into the bone. A thread with a high fusing point was inserted into the hole in the bone. An anchor of a somewhat greater thickness than that of the hole was then set up on the hole. The anchor was made of polypyrrole having a conductivity of 1,000 Ohm/square.

In a manner similar to Example 1, the anchor was also in this case subjected to a current by using an electrical cautery, and after softening up by the radiation energy pressed into the bone. After switching off the current, the polymer hardened and the anchor was locked to the bone, together with the thread.

EXAMPLE 4 (Bone Anchor)

In a modification of Example 3, the thread was passed through a transversally drilled hole in the anchor, the anchor was then inserted into the bone and fastened there by using an electrode. The tom-off tendon was then fastened using the thread. The thread was in this case held under a traction force. Thanks to the simultaneously switched-on current, the anchor partially fused and was under slight pressure glued to the thread, thus gaining a hold in the bone. After cooling within about 30 seconds, the traction force on the thread could be released. A knotting of the thread, which would otherwise have been necessary, could be omitted.

EXAMPLE 5 (Implantation of a Prosthesis)

In a dental implant made of titanium, the distal third was surrounded with a partially conductive thermoplastic material. For this purpose the implant was several times dipped into a solution of poly-D,L-lactide with 25% carbon black and dried between the dipping treatments. For insulating purposes, the upper two thirds of the surface were similarly coated with a low molecular weight quick-releasing poly-lactide-co-glycolide material.

The side turned away from the root tip was connected to a source of current. The implant was set up on the hole that had been pre-drilled undersized, and the current was switched on. As soon as the current flowed through the electrode into the implant, then through the polymer and again through the bone, the coating softened at the distal end, and the implant could then be pushed deeply into the hole under pressure. The solidification of the polymer in the bone led to a primary, load-resistant connection between the bone and the implant. The coating made of polylactide-co-glycolide degrades within a few days and allows the bones to grow on the titanium implant thereafter.

EXAMPLE 6 (Vascular clip)

The clip served to clamp-off blood vessels so as stop bleeding. It consisted essentially of two arms and a hinge. The arm was grasped with one clamp and the blood vessel was held locked in the same. The arms were subjected to current and pressed together. The current softened the hinge and allowed a bending of the clip. When the ends of the arms that were turned away from the hinge impinged on each other, a current also flowed at this point, and induced the fusing and the desired connecting of the two arms.

EXAMPLE 7 (Thread Clip)

The same application as described in Example 6 could also be employed for the fixation of threads so as to avoid knots. The clip had a length of 7 mm and consisted of two arms of equal length. The cross sectional diameter of the arms was 3×3 mm.

EXAMPLE 8 (Vertebral Implantation)

in a female patient with an osteoporotic compression fracture of the first lumbar vertebra, a hole of 4 mm diameter was drilled (under local anesthesia) from dorsal through the pedicles into the vertebral body (length of ab. 4 cm). A pin made of poly-D,L-lactide (of a diameter of 3.9 mm) filled with polypyrrole and with a resulting conductivity of 1,200 Ohm/square was passed from dorsal and still without any application of current through the hole. The pin itself was externally coated with a 0.5 mm thick insulating layer made of poly-D,L-lactide and a central longitudinal hole with a diameter of 0.6 mm. This longitudinal hole held a metal rod (of surgical steel) of a 0.5 mm diameter connected with the electrode. The electrode was then switched on and the pin was pushed into the vertebral body. Because the pin had no insulation on its tip, it made contact with the bone at that point and fused on the same. When pushing further on the pin (while holding the position of the electrode in the center, meaning pushing the pin into the depth like a thick-walled tube on the electrode) a filling of the vertebral body with the poly-D,L-lactide could be obtained. While fusing on, the pin was continuously losing its insulation at the tip, so that under a continuous fusing of the material, the pin could be pushed in further into the vertebral body. After a 2-minute cooling, the vertebral body was load-resistant and free of pain.

EXAMPLE 9 (Electrode Design)

This describes a particularly favorable arrangement of implant and electrode. The electrode is designed so as to be capable, as in Example 8, to be moved close to the location where the current is to be applied. In this case, however, the electrode has an insulation and is only circumferentially conductive for a length of 7 mm at its tip. In a manner similar to Example 8, the electrode was passed through a hollow pin (made of polylactide with 15% carbon black) and pushed through the pedicle into the vertebral body. The hollow pin could then be pushed over the electrode into the vertebral body with little resistivity. Contrary to the example 8, the pin is in this case not insulated against the pedicle wall and nevertheless fuses only at its tip, because the electrode emits current only at that point. The clinical result is the same as in Example 8. In an expanded form of embodiment the tip of the electrode could be equipped with a heat sensor to measure the heat generated there and to regulate it with the aid of a regulating commutation system at the current source. An excessive evolution of heat could thus be avoided.

EXAMPLE 10 (Defect Filling)

The same pin as described in Example 9 was also employed for the filling of a bone defect, in this case of a tibia head defect. For this purpose, in the patient with the tibia head fracture a 4 mm diameter hole was drilled from ventral through the corticalis toward the defect (length of 2 cm). The pin was then pushed through this hole into the medullary and the cancellous space of the bone while applying current, thus creating a stable bone as in a composite osteosynthesis. The screws subsequently inserted in this area provided an excellent hold in the fused polymer. It has been proven that the subsequent fusing-on of polymer in a recumbent osteosynthesis material or in recumbent prostheses leads to similarly stable conditions.

EXAMPLE 11 (Composite Osteosynthesis)

In the context of a collum femoris fracture in an osteoporosis condition, a dynamic hip screw was Implanted through the collum femoris, which had been modified as follows: it was internally fitted with an additional longitudinal borehole of 3 mm diameter, and at the threaded tip with 10 radial holes of 1 mm diameter which allowed a communication between the central borehole and the bone. A pin of 2.9 mm diameter insulated as in Example 9 was then inserted in this central borehole and subjected to a current from the rear. Under the effect of the current, the pin could be fused inside the screw, and the liquefied polymer penetrated through the holes outwardly into the bone, thus creating an augmentation of the bone wherein the implant locked. After the hardening of the polymer (2 minutes), the screw was load-resistant.

EXAMPLE 12 (Stent)

In the context of a vasodilatation, the radiologist inserts a heart catheter through a femoral access into the femoral vessels, and moves this catheter to a restricted kidney artery. A balloon with a folded-up stent around it, made of polypyrrole (diameter 1.5 mm, length 2 cm) is applied to the tip of the catheter. The balloon itself is conductive in a monopolar manner and lies inside the stent in a folded-up state. The balloon is then subjected to a current and the current flows through the stent to warm-up and soften the same. The balloon can then be blown up and the stent is expanded, until an adequate flow of blood is achieved. The current is switched off and the stent cools off, hardens (within 40 seconds) and keeps the vessel open.

EXAMPLE 13 (Memory Effect)

A bone anchor with an internal residual stress is produced by injection molding (PLA/polyaniline). In the now present cooled-off form, the anchor is straight (length 10 mm, diameter 3 mm). While using a thread passed through an eyelet in the upper third of the anchor, the anchor is pushed under soft pressure into a pre-drilled hole in the outer malleolus. Under the action of heat induced by the monopolar applied light, a relaxation of the anchor is initiated and the same bends over. This causes the anchor to jam in the hole of the bone, and gain a mechanical hold there. The thread on the anchor can thus be loaded after 30 seconds, and be employed for the reconstruction of a band.

EXAMPLE 14 (Nail Locking)

A femoral medullary nail is inserted into the femur for an osteosynthesis. However, in this 86-year old female patient the bone was distally too soft for a locking operation, the operator thus drilled a 4 mm hole from lateral through the corticalis toward the nail. A 3.5 mm pin made of a conductive synthetic material was pushed through the hole toward the nail. The pin was then subjected to a current in a mono-polar manner and pushed into the medullary canal, whereby it continuously fused away from the nail while filling up the medullary canal and embedding the nail. In order to properly distribute the implant material in the medullary canal, a relatively high level of energy (70 Watt) and a polymer of high thermal capacity were chosen, so as to prevent an excessively rapid cooling and solidification. After switching off the current, the nail was securely fixated at the center of the femur.

Figure 2A:
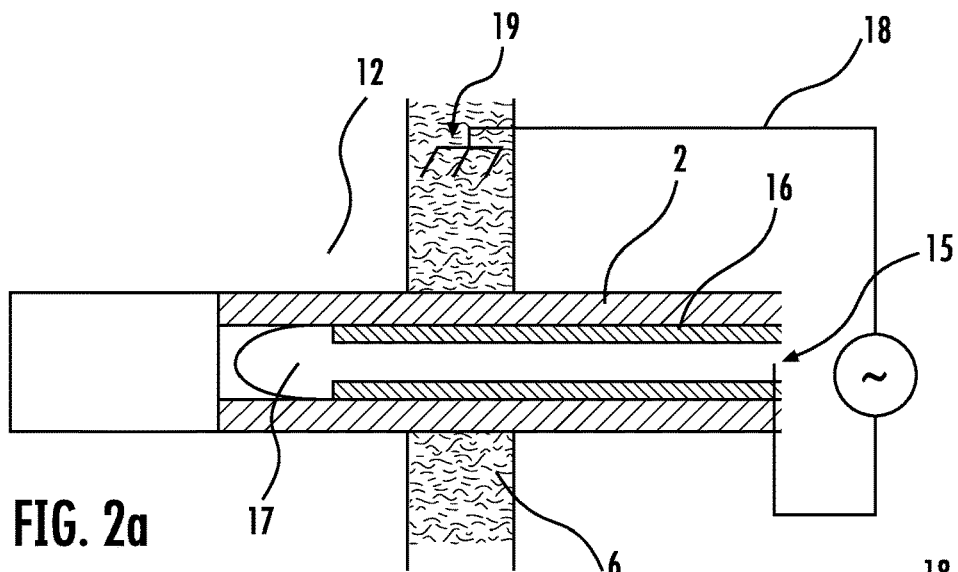
Figure 2B:
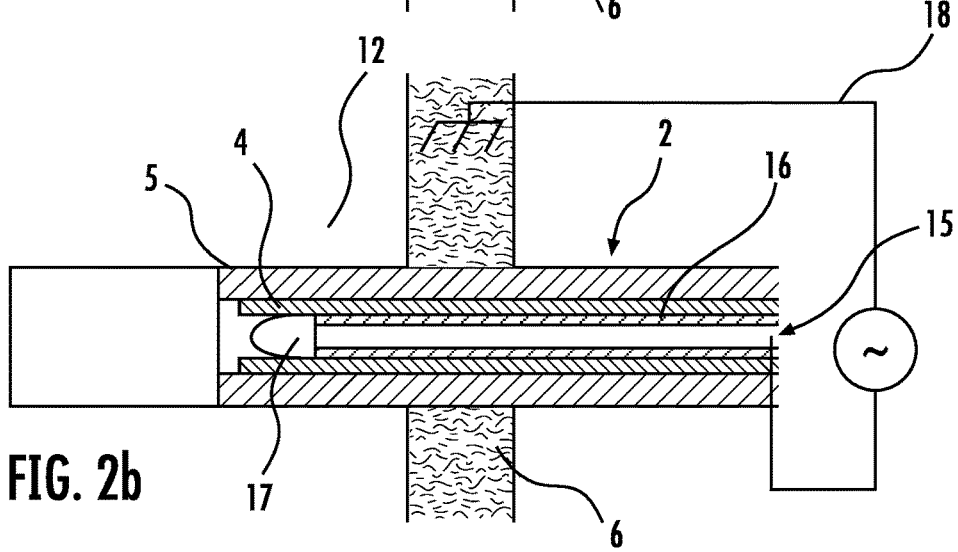
Figure 3B:
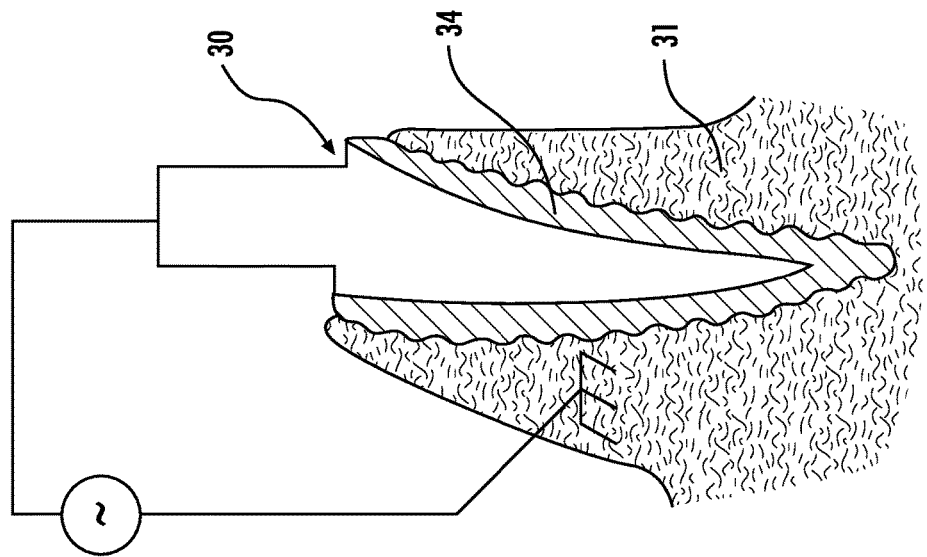
Figure 3A:
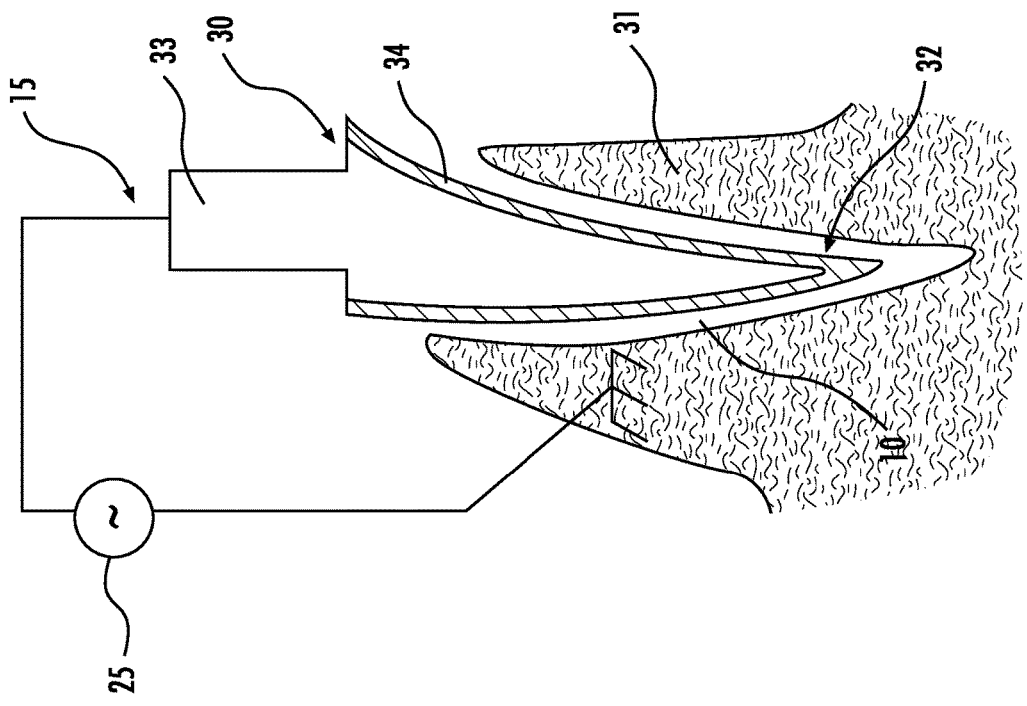
Figure 4:
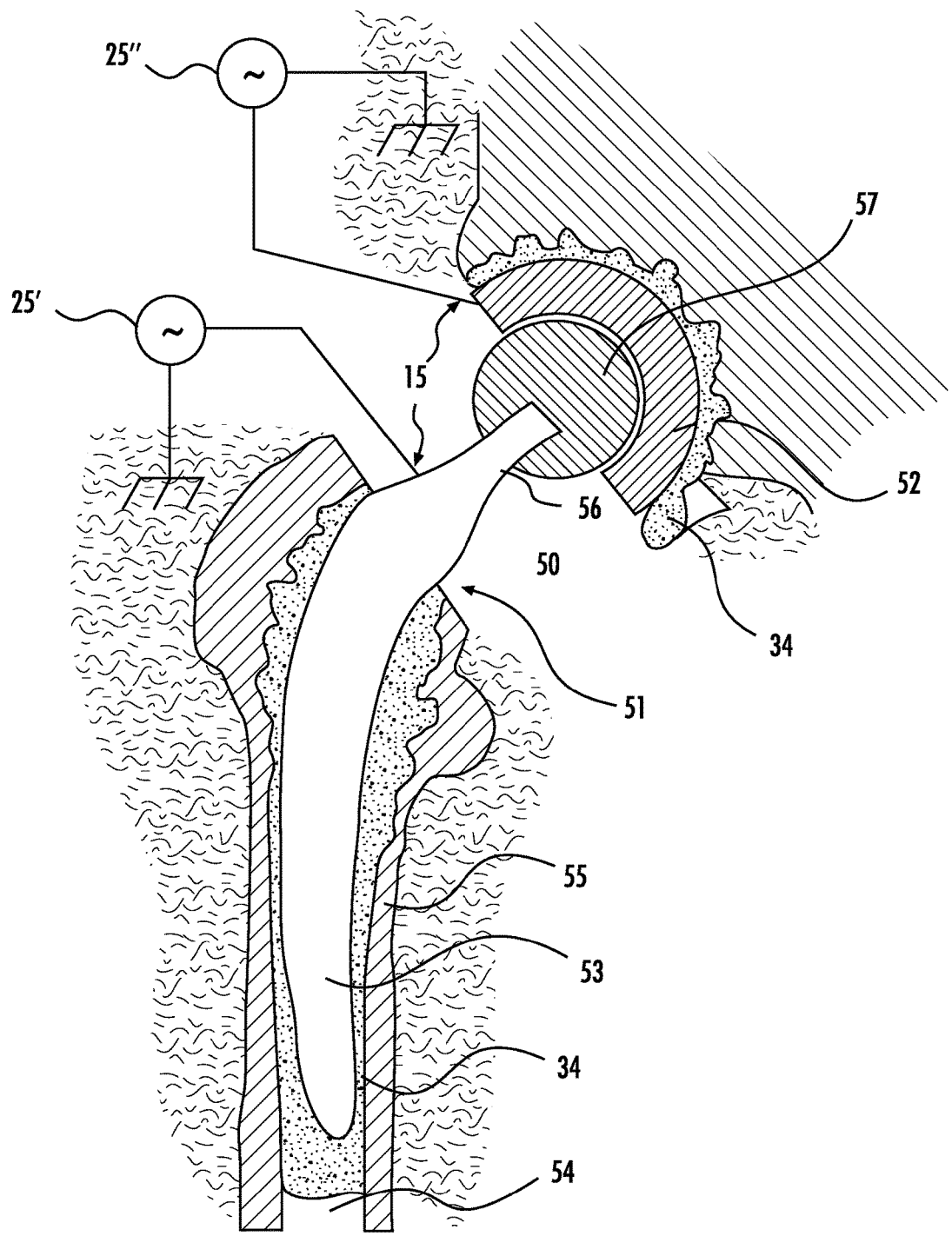
Figure 9A:
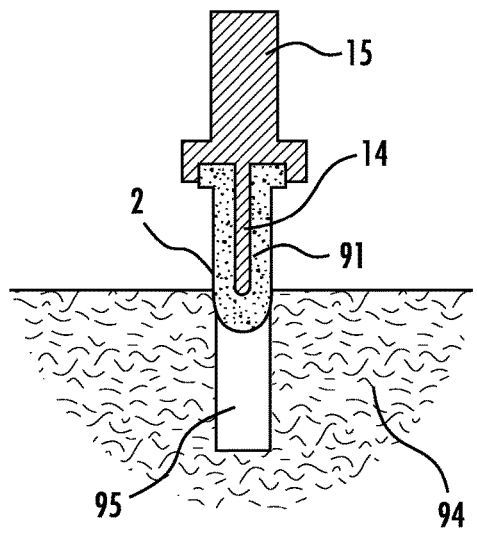
Figure 9B:
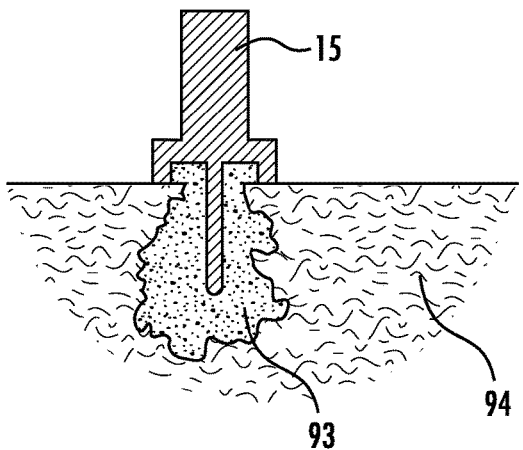
Figure 10:
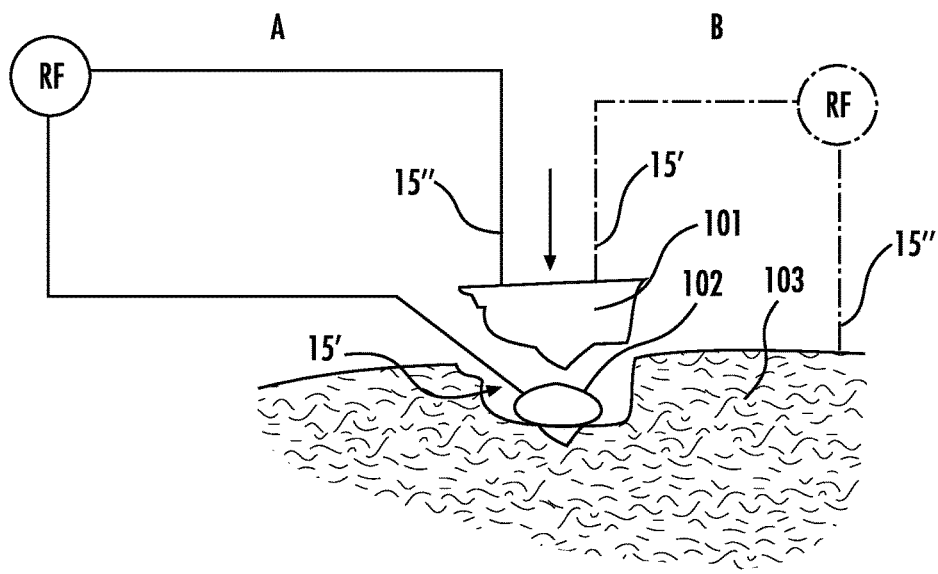
Figure 11A:
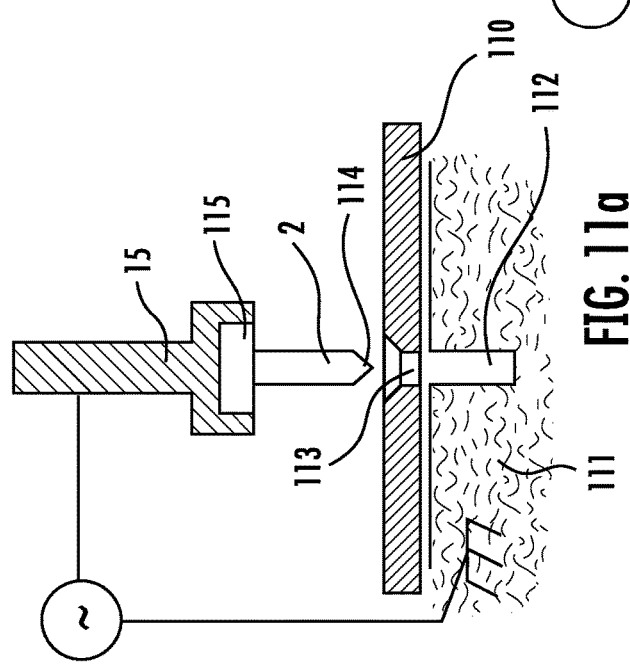
Figure 11B:
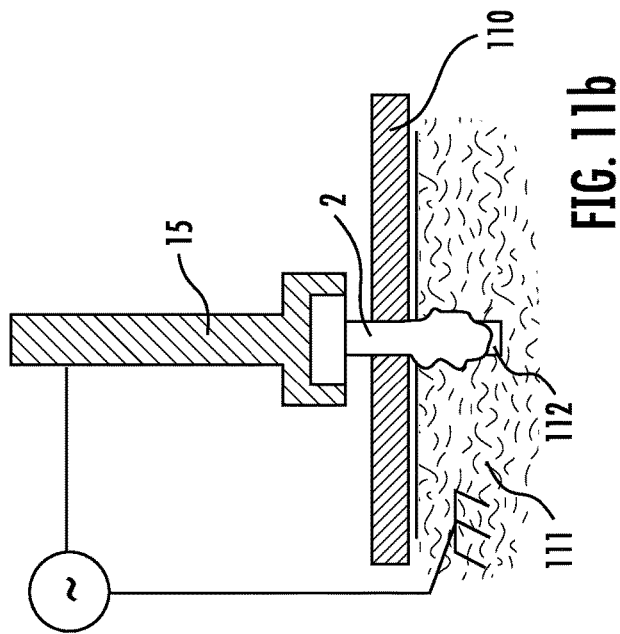
Figure 11C:
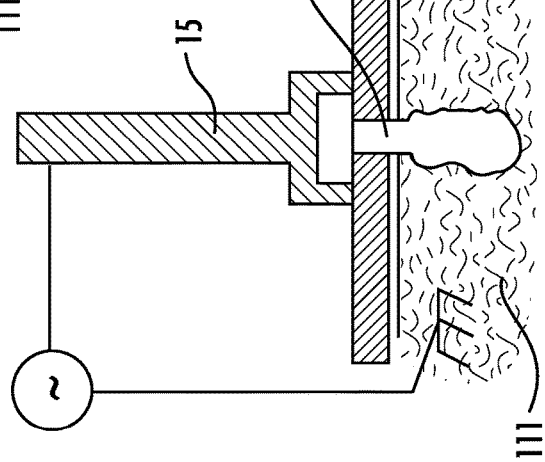
Figures 12, 13:
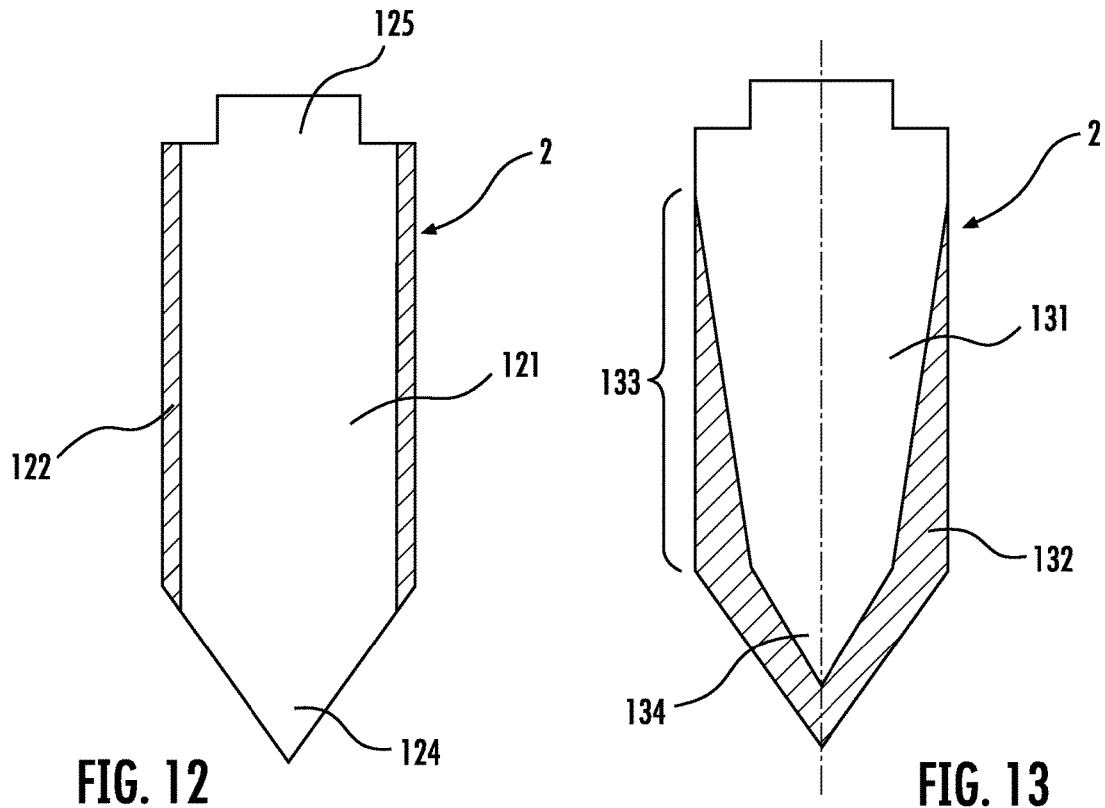
Figure 14:
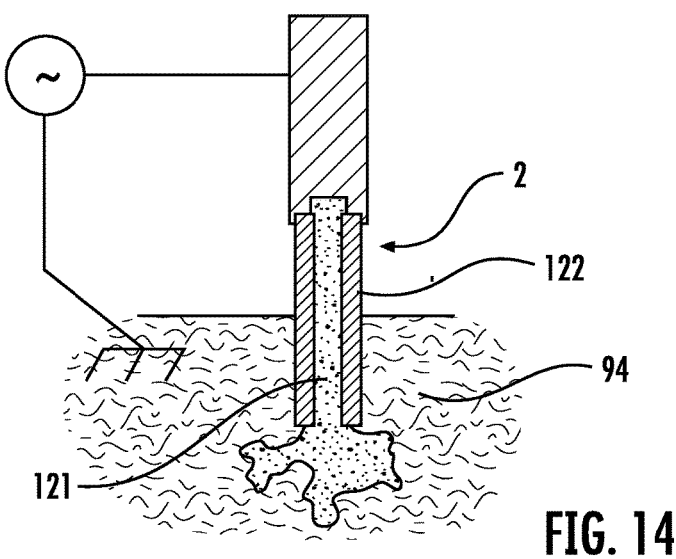
Figure 15A:
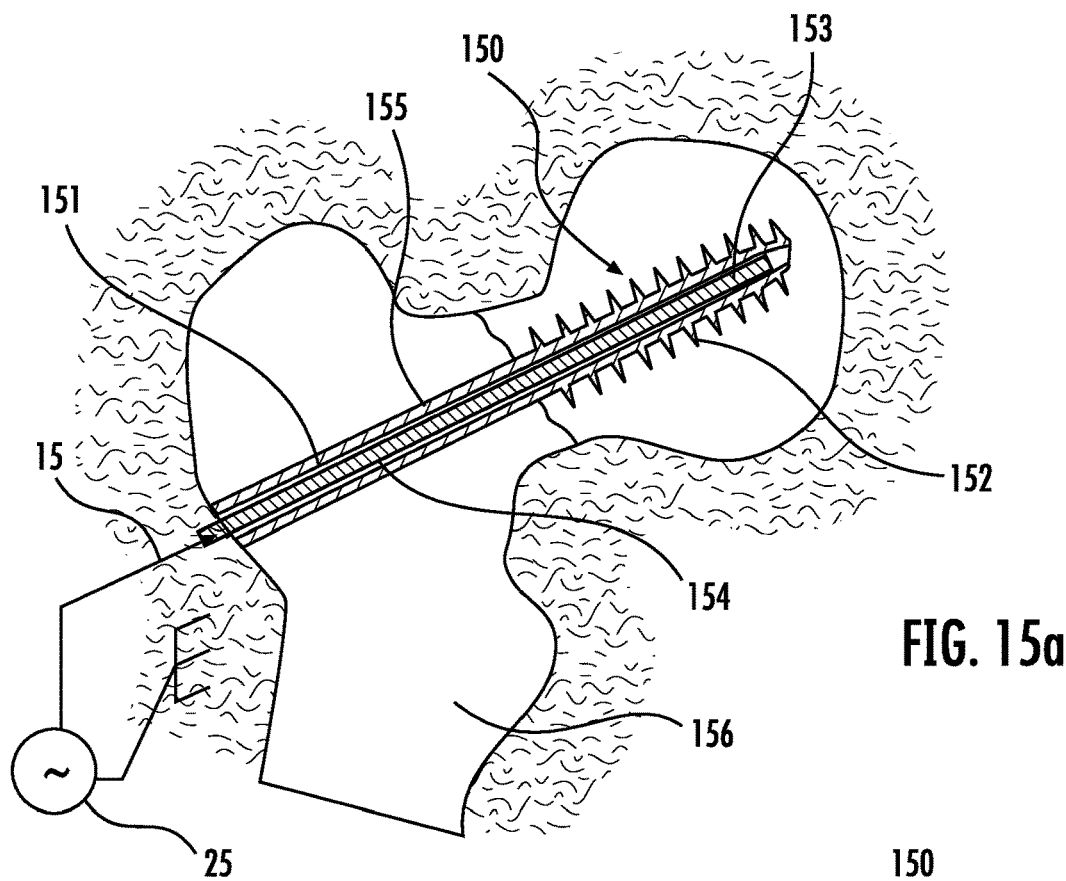

The invention and further developments of the invention will in the following, with the aid of partially simplified drawings of various examples of embodiments, be explained in greater detail. These show:

FIG. 1: A longitudinal section through a form of embodiment of the medical implant according to the invention;

FIG. 2*a*: A longitudinal section through another form of embodiment of the medical implant according to the invention;

FIG. 2*b*: A longitudinal section through a further form of embodiment of the medical implant according to the invention;

FIG. 3*a*: A cross section through another form of embodiment conformed as a dental implant of the medical implant according to the invention, prior to the fusing process;

FIG. 3*b*: A cross section through the form of embodiment according to FIG. 3*a*, after a completed implantation;

FIG. 4: A longitudinal section through another form of embodiment conformed as a hip joint prosthesis of the medical implant according to the invention, after a completed implantation;

FIG. 5a: A view of another form of embodiment of the medical implant according to the invention;

FIG. 5b: A view of the form of embodiment according to FIG. 5a, after a completed implantation;

FIG. 6a: A view of a further form of embodiment of the medical implant according to the invention;

FIG. 6b: A view of the form of embodiment according to FIG. 6a, after a completed implantation;

FIG. 7a: a view of another form of embodiment of the medical implant according to the invention;

FIG. 7b: A view of the form of embodiment according to FIG. 7a, after a completed implantation;

FIG. 8a: A section through another form of embodiment of the medical implant according to the invention;

FIG. 8b: A section through the form of embodiment according to FIG. 8a, after a completed implantation;

FIG. 9a: A section through another form of embodiment of the medical implant according to the invention;

FIG. 9b: A section through the form of embodiment according to FIG. 9a, after a completed implantation;

FIG. 10: A section through one more form of embodiment of the medical implant according to the invention;

FIG. 11a: A section through another form of embodiment of the medical implant according to the invention;

FIG. 11b: A section through the form of embodiment according to FIG. 11a during the implantation;

FIG. 11c: A section through the form of embodiment according to FIGS. 11a and 11b after a completed implantation;

FIG. 12: A section through another form of embodiment of the medical implant according to the invention;

FIG. 13: A section through a further form of embodiment of the medical implant according to the invention;

FIG. 14: A section through another form of embodiment of the medical implant according to the invention;

FIG. 15a: A section through one more form of embodiment of the medical implant according to the invention; and FIG. 15b: A section through the form of embodiment according to FIG. 15a after a completed implantation.

In the form of embodiment shown in FIG. 1, the medical implant according to the invention comprises a pin 2 with a peripheral insulating layer 1 and Is employed for an application in a vertebral plastic surgery (Example 9). A pin 2 made of a blend of polypyrrole and poly-D,L-lactide is inserted, from dorsal through a pre-drilled hole 10 into a pedicle of a vertebral body 12 to be treated.

The pin 2 itself is externally coated with a 0.5 mm thick insulating layer 1 made of poly-D,L-lactide and has a central longitudinal hole 13 with a diameter of 0.6 mm. This longitudinal hole 13 holds a metallic pin 14 (made of surgical steel) of a diameter of 0.55 mm, connected with the electrode 15. After inserting the pin 2, the current is switched on and the pin 2 is pushed, together with its connected electrode 15, into the vertebral body 12. As the pin 2 does not have an insulation at its tip, it contacts the bone at the point, and fuses on. A further pushing action on the pin 2 (while holding the position of the electrode 15 in the center, meaning that the pin 2 is pushed like a thick-walled tube into the depth on the electrode 15) can thus achieve a filling 3 of the vertebral body 12 with poly-D,L-lactide. After cooling off for 2 minutes, the vertebral body is load-resistant and pain-free. The current outflow occurs in a "monopolar" manner through the body of the patient to be treated, over a neutral conductor 18 (neutral electrode or grounding) on the skin or elsewhere on the patient's body via a large surface-area electrode, while the alternating current is typically fed in through the medical implant. In another form of embodiment, the pin 2 can also be realized without an insulating layer 1, and be pushed in through an insulating tube or an insulating hose inserted into the hole 10.

The form of embodiment illustrated in FIG. 2a differs from the form of embodiment represented in FIG. 1 only by another arrangement of the medical implant and the electrode 15, meaning by a different electrode design (Example 10). The electrode 15 is designed so that, like in FIG. 1, it can be conveyed close to the location where the current is to be applied. At this point, however, the electrode 15 has an insulation 16 with low-resistivity and is circumferentially conductive over a length of 7 mm only at it tip 17. In a manner similar to the form of embodiment in FIG. 1, the electrode 15 is inserted into the hollow pin 2 (made of polylactide with 15% carbon black) and pushed, together with the latter, through the pedicle into the vertebral body 12. In contrast to FIG. 1, at this point the pin 2 is not insulated against the pedicle wall and nevertheless fuses only at its tip, because the electrode 15 transmits current only at that point. In an expanded form of the embodiment (not drawn) the tip 17 of the electrode 15 if fitted with a heat sensor to measure the evolved heat and to regulate it through a regulating commutation at the source of the current. This can additionally prevent an excessive evolution of heat. The transmission of current occurs in a "monopolar" manner through the patient's body over the neutral conductor 18 (neutral electrode or grounding) on the skin 6, while using a large surface-area electrode. An alternative form of embodiment is represented in FIG. 2b, which differs from that in FIG. 2a only by the fact that at this point the pin 2 comprises an internal bushing 4 surrounding the electrode 15 and made of a conductive polymer with a low resistivity, and coaxially an external bushing 5 made of a conductive polymer with a higher resistivity. The external bushing 5 is also closed at its ending inserted into the vertebral body 12.

Based on its higher resistivity, the external busing 5 warms-up and deforms while the current flows through the pin 2.

The form of embodiment represented in the FIGS. 3a and 3b comprises a dental implant 30 made of titanium, whose section to be inserted into the bone 31 is surrounded by a layer 34 made of a conductive thermoplastic material. For this purpose, the dental implant section 30 to be inserted into the bone 31 is repeatedly dipped into a solution of poly-D, L-lactide with 25% carbon black and dried between the dipping treatments. The uncoated end 33 turned away from the distal end 32 is connected to a source of current. The dental implant 30 is set up on the hole 10 pre-drilled undersize, and the current is switched on (FIG. 3a). As soon as the transmission of current occurs through the electrode 15, the dental Implant 30, the layer 34 formed of a polymer and the bone 31, the layer 34 softens beginning from the distal end 32, and the dental implant 30 can then be pushed into the depth of the hole 10 under pressure. While pressing the dental implant 30 into the hole 10, the thermoplastic material forming the layer 34 is pressed into the interspaces in the bone 31, so as to generate a mechanical connection between the dental Implant 30 and the bone 31. The solidification of the polymer, meaning of the layer 34 in the bone 31, leads to a primary, load-resistant connection between the bone 31 and the dental implant 30 (FIG. 3b).

The form of embodiment represented in FIG. 4 comprises a medical implant conformed as a hip joint prosthesis 50. The hip joint prosthesis 50 comprises an electrically conductive metallic femoral component 51, whose shaft 53 to be inserted in the medullary canal 54 of the femur 55 is, like in the form of embodiment shown in the FIGS. 3a and 3b, coated with a layer 34 made of a conductive polymer, and an equally conductive metallic articular cup 52 which is, at its outer surface contacting the glenoid cavity, coated with a layer 34 made of a conductive polymer. The femoral component 51 is at its uncoated neck 56 or its articular head 57 connected to a current source 25'. The articular cup 52 is connected to a second current source 25" in a similar manner. The femoral component 51 in inserted into the medullary canal 54 pre-drilled with an undersized hole, and the articular cup 52 is inserted in the glenoid cavity. As soon as the current is switched on and the transmission of current takes place across the electrode 15, the femoral component 51, the layer 34 made of a polymer and the femur 55, the layer 34 softens due to an internal evolution of heat. In the second current circuit, the transmission of current occurs over a second electrode 15, the articular cup 52 and the hip bone, whereby the layer 34 on the outside of the articular cup 52 softens due to the internal evolution of heat. The femoral component 51 can now be pushed into the depth of the medullary canal 54 under pressure. When pressing the femoral component 51 into the medullary canal 54, the thermoplastic material forming the layer 34 is pressed into the interspaces in the bone, so that a mechanical connection is generated between the femoral component 51 and the bone. In a similar manner the articular cup 52 is pushed into the glenoid cavity, whereby the softened layer 34 on the articular cup 52 is pressed into the interspaces in the bone, and a mechanical connection is likewise generated between the articular cup 52 and the bone. The solidification of the polymer, meaning of the layers 34 on the femoral component 51 in the femur 55 and on the articular cup 52 in the glenoid cavity, leads to a primary, load-resistant connection between the bone and the hip joint prosthesis 50.

The FIGS. 5a and 5b show a further form of embodiment, where the pin 2 is, through an appropriate production process such as for instance injection molding, provided with a residual stress and presents a length L and a diameter D in a cooled-down condition (FIG. 5a). Thanks to the warming-up of the entire pin 2 through a flow of current between the poles A, B, the thermoplastic material relaxes and the pin 2 shortens and increases in diameter (FIG. 5b), which leads a fixation in or on the surrounding tissue.

In the form of embodiment illustrated in the FIGS. 6a and 6b, the medical implant is conformed as a clip 60. The clip 60 is conformed to a U-shape and comprises two arms 61, 62, whose free ends 63 each comprise an element 64 made of a conductive polymer. These elements 64, which are thicker than the arms 61, 62, are connected through electrodes 15', 15" to a current circuit (FIG. 6a). After switching on the current source, the clip 60 is pressed together, meaning that the two elements 64 are pressed together. Thanks to the current flow, the two elements 64 are warmed-up and soften at the contact points which are leaning together, and can thus be joined by applying pressure and fusing them together (FIG. 6b).

The clip 70 shown in the FIGS. 7a and 7b differs from the clip shown in the FIGS. 6a and 6b only by the fact that the clip 70 is produced from a single piece of conductive polymer. The arms 71, 72 are grasped with a clamp 74, subjected to current through a respective electrode 15', 15" and pressed together. Thanks to the current flow, the hinge 73 connecting the arms 71, 72 softens and allows a bending of the clip 70. When the ends of the arms 71, 72 turned away from the hinge 73 are impinging on each other, current is also transmitted at this point, which leads to a fusing and the desired connecting of the two arms 71, 72 at their ends which are thickened with respect to the arms 71, 72.

In the form of embodiment illustrated in the FIGS. 8a and 8b, the medical implant comprises a thread 80 consisting of a material with a high point of fusion and an anchor 83 made of a conductive polymer. The thread 80 is to be fixated to the bone 81 so that the thread 80 locks for instance a tendon or another bone element. For this purpose, a hole 82 having a diameter of 3 mm Is drilled to a depth of 15 mm into the bone 81. The thread 80 is then inserted in this hole 82 in the bone 81. An anchor 83 having a slightly greater diameter than the hole 82 is then set up on the hole 82. In a manner similar to Example 1, the anchor 83 is also subjected to current through an electrical cautery, and after being softened by the flow of current, pressed into the bone 81. After switching off the current, the conductive polymer solidifies and the anchor 83, together with the thread 80, is fixated in the bone 81.

The form of embodiment shown in the FIGS. 9a, 9b is suitable for the filling of defects in the bone 94. In a manner similar to the form of embodiment according to FIG. 1, a pin 2 is used which has a central, enclosed hollow space 91 at the tip of pin 2 to receive a metallic pin 14 connected with an electrode 15. The metal pin 14 can be removed again after the pin 2 has fused, or can also be produced from a resorbable material. In order, for instance, to fill a tibia head defect in a patient affected by a tibia head fracture, a hole 95 with a diameter of 4 mm is drilled from ventral, through the corticalis, up to the defect (length of 2 cm). The pin 2, together with the metallic pin 14, is then pushed through this hole 95 into the medullary canal and into the cancellous space of the bone while applying a current and thus creating, as in a composite osteosynthesis, a stable bone by a fusing of the pin 2 to a filling 93. The screws (not shown here) subsequently inserted into this filling 93 provide an excellent hold in the initially fused and then hardened polymer material.

FIG. 10 illustrates a form of embodiment wherein the polymer of the medical implant is conformed as a pearl 102. This pearl 102 can be inserted into the hollow space that arises when a bone fragment 101 is broken out of a bone 103. The fitting of the bone fragment 101 into the hollow space and the connecting of the bone fragment 101 with the bone 103 by fusing the pearl 102 and pressing the polymer into the interspaces in the bone fragment 101 and the bone 103 can be achieved through two variants A and B. In the variant A, a first electrode 15' is connected to the pearl 102, while a second electrode 15" fastened to the bone fragment 101. After switching on the current source, the transmission of current takes place from the current source over the first electrode 15' and the pearl 102 while warming it up and over the second electrode 15". In the variant B the first electrode 15' is fastened to the bone fragment 101, while the second electrode 15" is fastened to the bone 103. At this point, after switching on the current source the transmission of current occurs over the first electrode 15', the bone fragment 101, the pearl 102 while warming it up, the bone 103 and the second electrode 15".

The form of embodiment shown in the FIG. 11a-11c comprises a pin 2 made of a conductive polymer suitable for fixating a bone plate 110 on a bone 111. The bone plate 110 is a resorbable osteosynthesis plate with a thickness of 1 mm, made of a poly-D,L-lactide. In order to fixate the fracture, the bone plate 110 is applied to the bone fragments to be fixated, and the holes 112 needed for its fixating to the bone 111 are drilled into the bone 111. This example shows a bone plate 110 fitted with screw holes 113 for 2 mm screws. The holes 112 drilled into the bone 111 have a diameter of 1.5 mm. The electrically conductive pin 2 is conveyed with its tip 114 to be inserted into the bone 111 through the screw hole 113 in the bone plate 110, set up on the hole 112 which has been pre-drilled into the bone 11, and subjected to a current. The transmission of current through the electrically conductive pin 2 warms-up the same. Because the largest electrical voltage drop occurs at the transition between the bone 111 and the pin 2, the greatest heat arises at this point in pin 2, which softens up the pin 2, especially at its surface. By exerting a pressure on the electrode 15, the pin 2 is pushed Into the hole 112 which has been pre-drilled into the bone 111, and the thermoplastic material flows into the available intra-trabecular interspaces in the cancellous bone (FIG. 11b). After switching off the current the polymer cools off again and solidifies. The head 115 of the pin 2, which has a diameter larger than the screw hole 113 in the bone plate, now locks the bone plate 110 (FIG. 11c).

The FIGS. 12 and 13 each show a pin 2 which comprises a core 121, 131, made of a material of low resistivity, for instance of a metal or of a conductive polymer and a coating 122, 132 made of an electrically conductive polymer with a higher resistivity. The coating 122 in FIG. 10 is conformed like a bushing and extends over the cylindrical portion 123 of the pin 2. The tip 124 of the pin 2 and the axially opposite rear end 125, which can be connected to an electrode, are conformed without a coating 122. The coating 132 in FIG. 13 is only partially applied on a frontal section 133 of the pin 2, and encloses the tapering section 133 of the pin 2 including its tip 134. A pin 2 conformed according to the FIG. 12 or 13 allows a selective warming up of a thermoplastic material, so as to achieve a deformation. In FIG. 12 the pin 2 will warm-up at the thin tip 124, because the bushing acts as an insulator and the current flows out through the tip. In FIG. 13 the pin 2 will warm up and deform at the zone with a larger resistivity in the current circuit, meaning on the coating 132.

FIG. 14 shows the application of a pin according to FIG. 12, for the filling of a defect in a bone 94 as described in the FIGS. 9a and 9b.

Figure 15B:
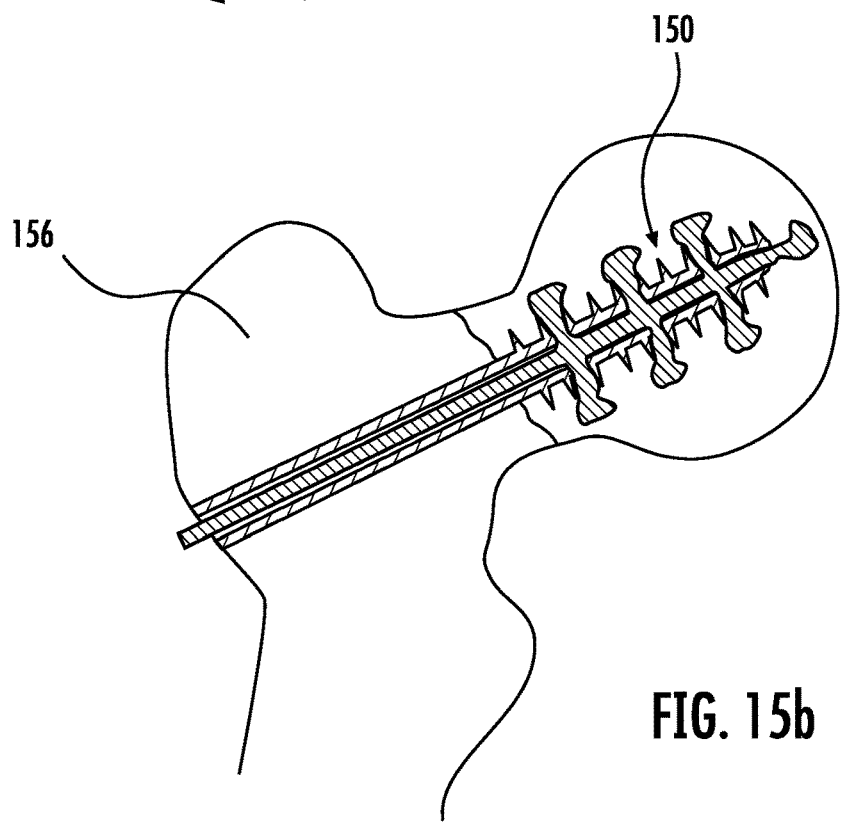

The FIGS. 15a and 15b illustrate a form of embodiment where the medical implant comprises a dynamic hip screw 150 and a pin 2 made of a conductive polymer. The dynamic hip screw 150 has a hollow shaft 151 with a threaded borehole 152 on its frontal end extending up to the head of the hip joint. The region of the threaded borehole 152 has radial perforations 153 that radially perforate the shaft 151 between its central hollow space 154 and its perimeter. Apart from the perforations 153, the hollow space 154 is fitted with an insulating coating 155. In the context of a collum femoris fracture, in the presence of an osteoporosis the dynamic hip screw 150 is implanted through the collum femoris. As described in Example 9, an isolated pin 2 of a diameter of 2.9 mm diameter is then inserted into the central hollow space 154, and connected, through an electrode 15, at its rear end opposite the threaded borehole 152 of the dynamic hip screw 150, to a current source 25. Under the application of current, the pin 2 thus fuses inside the hip screw 150 and the liquefied polymer penetrates through the perforations 153 toward the outside into the bone 156, thus creating an augmentation of the bone 156 in which the implant locks up. After the solidification of the polymer, the hip screw 150 is load-resistant (FIG. 15b).

The invention claimed is:

1. A method for osteosynthesis comprising:
positioning, at an implantation site, a medical implant comprising a biocompatible polymer element being heat-softenable responsive to application of an electric current to the biocompatible polymer element, wherein the biocompatible polymer element is electrically conductive, wherein the biocompatible polymer element comprises different resistivity throughout a volume of the biocompatible polymer element that allows selectively shaping the implant;
heating and softening the biocompatible polymer element of the medical implant by passing an electric current therethrough; and
introducing the heated and softened biocompatible element into the implantation site.

2. The method of claim 1, wherein the biocompatible polymer element has a softening temperature above 40° C.

3. A method for osteosynthesis comprising:
positioning, at an implantation site, a bone fixation device comprising a bone plate with at least one through hole;
positioning a medical implant, which is oversized with respect to the at least one through hole, adjacent the at least one through hole, the medical implant comprising a biocompatible polymer element being heat-softenable responsive to application of an electric current to the biocompatible polymer element, wherein the biocompatible polymer element is electrically conductive, wherein the biocompatible polymer element comprises different resistivity throughout a volume of the biocompatible polymer element that allows selectively shaping the implant;
heating and softening the biocompatible polymer element of the medical implant by passing an electric current therethrough;
fixing the bone fixation device to a bone by inserting the heated and softened biocompatible element into the at least one through hole.

4. The method of claim 3, wherein the biocompatible polymer element comprises an electrically conductive polymer.

5. The method of claim 3, wherein the biocompatible polymer element has a softening temperature above 40° C.

6. The method of claim 3, comprising using a patient's body as an electrode to supply electric current to the biocompatible polymer element of the medical implant.

7. A method for osteosynthesis comprising:
positioning, at an implantation site, a medical implant comprising a biocompatible polymer element being heat-softenable responsive to application of an electric current to the biocompatible polymer element, wherein the biocompatible polymer element is electrically conductive and uses a patient's body as an electrode to supply electric current to the biocompatible polymer element of the medical implant;
heating and softening the biocompatible polymer element of the medical implant by passing an electric current therethrough; and
introducing the heated and softened biocompatible element into the implantation site.

* * * * *